(12) United States Patent
Frost et al.

(10) Patent No.: US 6,472,169 B1
(45) Date of Patent: Oct. 29, 2002

(54) BIOCATALYTIC SYNTHESIS OF SHIKIMIC ACID

(75) Inventors: John W. Frost; Karen M. Frost; David R. Knop, all of Okemos, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/676,609

(22) Filed: Sep. 30, 2000

Related U.S. Application Data

(63) Continuation-in-part of application No. 09/240,440, filed on Jan. 29, 1999.

(51) Int. Cl.[7] ............................. C12P 1/00; C12P 15/00; C12P 7/22; C12N 1/20; C07H 21/04
(52) U.S. Cl. ......................... 435/41; 435/127; 435/156; 435/189; 435/193; 435/232; 435/252.3; 435/320.1; 435/822; 435/849; 435/911; 435/940; 536/23.2
(58) Field of Search .......................... 435/41, 127, 156, 435/189, 193, 232, 252.3, 320.1, 822, 849, 911, 940; 536/23.2

(56) References Cited

FOREIGN PATENT DOCUMENTS

| WO | WO 94/14955 | * 7/1994 |
|---|---|---|
| WO | 96 34961 | 11/1996 |

OTHER PUBLICATIONS

EP 99 95 6926 Supplementary European Search Report.

* cited by examiner

*Primary Examiner*—Tyakchand Saidha
(74) *Attorney, Agent, or Firm*—Harness, Dickey & Pierce, P.L.L.C.

(57) ABSTRACT

A bioengineered synthesis scheme for the production of shikimic acid from a carbon source is provided. Methods of producing shikimic acid from a carbon source based on the synthesis scheme are also provided.

21 Claims, 8 Drawing Sheets

BIOCATALYTIC SYNTHESIS OF SHIKIMIC ACID

This application is a continuation-in-part of Ser. No. 09/240,440 filed Jan. 29, 1999.

SPONSORSHIP

Work on this invention was sponsored in part by the United States Department Of Agriculture, Grant No. 95-37500-1930, the National Science Foundation Grant No. CHE963368 amendment 002 and the National Institutes of Health, Grant No. GM58684. The Government may have certain rights in the invention.

FIELD OF THE INVENTION

The present invention is related to the production of shikimic acid and more specifically, to methods of producing shikimic acid from bioconversion of a carbon source.

BACKGROUND OF THE INVENTION

Shikimic acid is an attractive chiral synthon with its highly functionalized, six-membered carbocyclic ring and multiple asymmetric centers. A metabolic intermediate of aromatic amino acid biosynthesis, shikimic acid has emerged as an essential chiral starting material in the synthesis of neuraminidase inhibitors effective in the treatment of influenza. Kim. C.U. et al., *J. Am. Chem. Soc.* 119:681 (1997); Rohloff, J.C. et al., *J. Org. Chem.* 63:4545 (1998). Chiral, as well as aromatic chemicals, can also be synthesized from shikimic acid. For example, acid catalyzed dehydration of shikimic acid affords p-hydroxybenzoic acid (Eykmann, J.F., *Ber. Dtch. Chem. Ges.* 24:1278 (1891)). p-Hydroxybenzoic acid, which has an annual production of $7 \times 10^6$ kg, is the key precursor to parabens and a monomer used in the synthesis of liquid crystal polymers. Shikimic acid has also recently been used as the starting point for synthesis of a large combinatorial library of molecules. Tan, D.S. et al., *J. Am. Chem. Soc.* 120:8565 (1998).

Shikimic acid is obtained via tedious multi-step isolation procedures from plants. Unfortunately, current isolation of shikimic acid from the fruit of Illicium plants (Haslem, E., *Shikimic Acid: Metabolism and Metabolites*, Wiley & Sons, New York, pp. 40–42 (1993)) precludes its use in kilogram-level synthesis.

Therefore, it would be desirable to provide a method to produce large quantities of shikimic acid. It would also be desirable if such a method were cost-efficient, using inexpensive starting materials. It would further be desirable if the method employed non-toxic compounds and was environmentally benign.

SUMMARY OF THE INVENTION

A bioengineered synthesis scheme for production of shikimic acid from a carbon source is provided. In one embodiment, the bioconversion methods of the present invention comprise the microbe-catalyzed conversion of a carbon source to shikimic acid. The method comprises selecting a host cell, introducing into the host cell the ability to convert the carbon source to shikimic acid in the host cell, impeding in a pathway of the host cell the conversion of shikimic acid to shikimate-3-phosphate and culturing the host cell in the carbon source. The methods further comprise contolling the molar ratio of shikimic acid to quinic acid during culturing. As shown in the synthesis scheme of FIG. 1, the microbe-catalyzed conversion step of the present invention requires four enzymes which may be provided by a recombinant microbe. In a preferred embodiment, the recombinant microbe is *Escherichia coli* designed to cause reduction of 3-dehydroshikimate to shikimic acid and to inhibit any further conversion of shikimic acid along the aromatic amino acid biosynthetic pathway.

In another embodiment, methods are provided for increasing the production of shikimic acid with the recombinant microbes of the present invention. In a preferred embodiment, the methods comprise blocking the phosphoenolpyruvate carbohydrate phosphotransferase system of the host cell and introducing into the host cell the ability to transport glucose into the cell. In an alternate preferred embodiment, the methods comprise introducing into the host cell the ability to convert pyruvate to phosphoenolpyruvate. In a further preferred embodiment, the host cell is *E. coli* B. Production of shikimic acid in the methods of the present invention is increased when this strain of *E. coli* is used as the host cell.

The biocatalytic synthesis method for shikimic acid provided herein, is believed to be environmentally benign, economically attractive, and utilizes abundant renewable sources as a starting material.

Additional objects, advantages, and features of the present invention will become apparent from the following description and appended claims, taken in conjunction with the accompanying drawing.

BRIEF DESCRIPTION OF THE DRAWINGS

The various advantages of the present invention will become apparent to one skilled in the art by reading the following specification and subjoined claims and by referencing the following drawing in which:

DETAILED DESCRIPTION OF THE PREFERRED EMBODIMENTS

Figure 1:
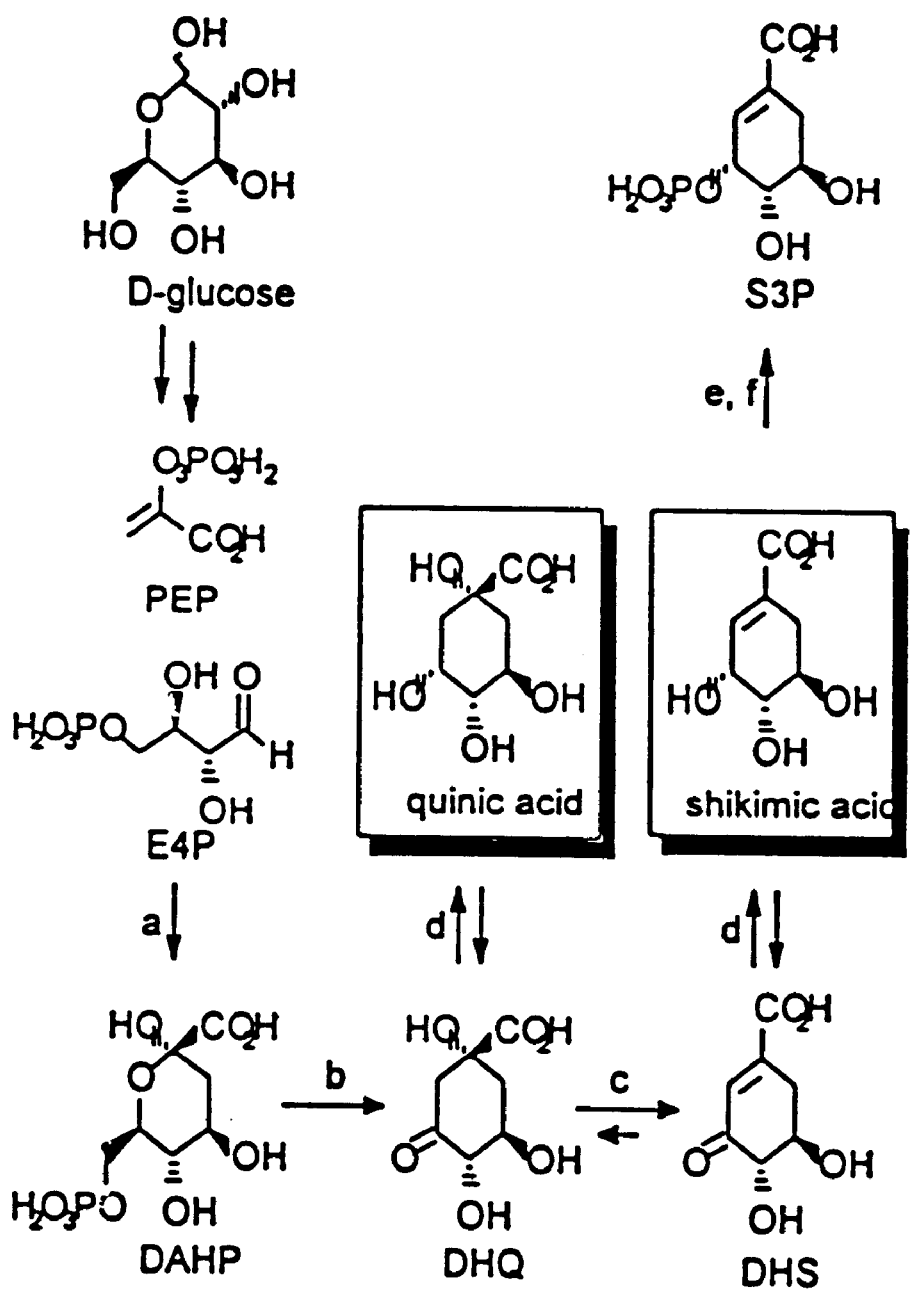
FIG. 1 is a schematic illustrating the bioengineered synthesis scheme of the present invention for producing shikimic acid.

A bioengineered synthesis scheme for the production of shikimic acid from a carbon source is provided herein. Methods of producing shikimic acid from a carbon source based on the synthesis scheme are also provided.

In one embodiment, a method is provided wherein the carbon source is converted to shikimic acid by a recombinant microbe. Manipulation of the common aromatic amino acid biosynthetic pathway of the microbe results in a significant production of shikimic acid when the recombinant microbe is cultured in the presence of a carbon source. The carbon source is converted to 3-deoxy-D-arabino-heptulosonate-7-phosphate (DAHP) which is subsequently converted by 3-dehydroquinate synthase to 3-dehydroquinate (DHQ) which is then dehydrated to 3-dehydroshikimate (DHS) by 3-dehydroquinate dehydratase (c, FIG. 1). 3-dehydroshikimate is converted to shikimic acid by shikimate dehydrogenase (d, FIG. 1). Metabolism of shikimic acid may be prevented by blocking or impeding shikimate kinase activity (e,f, FIG. 1), thus allowing for the accumulation of significant amounts of shikimic acid. In a preferred embodiment, the microbe will be unable to reabsorb shikimic acid from the medium due to a mutation in shikimate uptake (shiA). Thus, once formed, shikimic acid can not be converted into quinic acid or any other molecule in the pathway.

In a further embodiment, methods are provided for increasing the production of shikimic acid from a carbon source in which the carbon source is converted to shikimic acid by a recombinant microbe. In a preferred embodiment, shikimic acid production is increased by recycling pyruvic acid back to phosphoenolpyruvate (PEP). In another preferred embodiment, the phosphoenolpyruvate carbohydrate phosphotransferase (PTS) system is inactivated and glucose transfer is controlled instead by the glf-encoded glucose facilitator and glk-encoded glucokinase.

The bioconversion methods of the present invention are carried out under conditions of time, temperature, pH, nutrient type and concentration, aeration conditions, and controlled glucose concentrations, to provide maximal conversion of the carbon source to shikimic acid. As described in detail in the Specific Examples, in a preferred embodiment, a fed-batch fermentor is used to convert the carbon source to shikimic acid, followed by isolation of the shikimic acid from the fermentation broth by ion-exchange chromatography. The batch fermentor process and chromatography methods are known to those skilled in the art.

As used herein, the phrase "carbon source" is meant to include biomass derived carbon sources including, but not limited to, xylose, arabinose, glycerol, glucose and the intermediates in the Krebs cycle (e.g., dicarboxylic acids), either alone or in combination. In a preferred embodiment, the carbon source is glucose. The carbon source may be derived from renewable resources such as, without limitation, corn, sugar beets and sugar cane.

In another embodiment, the recombinant microbe employed in the methods of the present invention is $E.$ $coli$. In a preferred embodiment, the $E.$ $coli$ comprises an aroB cassette inserted into the serA locus and disruption of the aroL and aroK loci (e and f, FIG. 1). This recombinant $E.$ $coli$ may further comprise a plasmid carrying aroF$^{FBR}$, aroE and serA gene inserts. Shikimic acid accumulates due to the absence of the aroL- and arok-encoded isozymes of shikimate kinase which catalyze the conversion of shikimic acid to shikimate-3-phosphate. The second copy of aroB increases the catalytic activity of 3-dehydroquinate synthase, thereby introducing into the host cell the ability to increase the production of shikimic acid. Dell, K.A. et al., $J.$ $Am.$ $Chem.$ $Soc.$ 115:11581 (1993). It will be appreciated, however, that the aroL and arok loci mutations are not essential and are employed to provide greater production of shikimic acid.

In a preferred embodiment, the recombinant $E.$ $coli$ comprises plasmid pSC5.112B carrying aroF$^{FBR}$, SerA, aroE and glk gene inserts. The aroF$^{FBR}$ gene insert encodes a mutant 3-deoxy-D-arabino-heptulosonate-7-phosphate synthase isozyme (a, FIG. 1) insensitive to feedback inhibition by aromatic amino acids or other aromatic molecules which increases carbon flow into the common aromatic amino acid biosynthetic pathway. Amplified shikimate dehydrogenase resulting from expression of aroE compensates for the enzyme's feedback inhibition by shikimic acid. Pittard, J. et al., $J.$ $Bacteriol.$ 92:1070 (1966); Brown, K.D. et al., $Biochim.$ $Biophys.$ $Acta.$ 428:550 (1976). Due to a mutation in the $E.$ $coli$ genomic serA locus required for L-serine biosynthesis, growth in minimal salts medium and plasmid maintenance follows from expression of plasmid-localized serA. The plasmid serA insert thus allows microbial growth in minimal salts medium, distinguishing the microbes.

In a preferred embodiment, the recombinant $E.$ $coli$ comprises plasmid pKD12.112 carrying aroF$^{FBR}$, serA and aroE inserts. The aroF$^{FBR}$ gene insert encodes a mutant 3-deoxy-D-arabino-heptulosonate-7-phosphate synthase isozyme (a, FIG. 1) insensitive to feedback inhibition by aromatic amino acids or other aromatic molecules which increases carbon flow into the common aromatic amino acid biosynthetic pathway. Amplified shikimate dehydrogenase resulting from expression of aroE compensates for the enzyme's feedback inhibition by shikimic acid. Pittard, J. et al., $J.$ $Bacteriol.$ 92:1070 (1966); Brown, K.D. et al., $Biochim.$ $Biophys.$ $Acta.$ 428:550 (1976). Due to a mutation in the $E.$ $coli$ genomic serA locus required for L-serine biosynthesis, growth in minimal salts medium and plasmid maintenance follows from expression of plasmid-localized serA. The plasmid serA insert thus allows microbial growth in minimal salts medium, distinguishing the microbes.

In another embodiment, the $E.$ $coli$ comprises plasmid pKD12.138. This plasmid is derived from and carries the same gene inserts as pKD12.112 as well as a tktA gene insert encoding for transketolase. Transketolase catalyzes formation of D-erythrose 4-phosphate, an unstable aldose phosphate typically maintained at vanishingly low concentrations in the cell. Elevated expression of transketolase provides additional D-erythrose 4-phosphate for subsequent condensation with phosphoenolpyruvate to form 3-deoxy-D-arabino-heptulosonate-7-phosphate, the first committed intermediate of aromatic amino acid biosynthesis.

In a further embodiment, the $E.$ $coli$ comprises plasmid pKD15.071B. This plasmid is derived from and carries the same gene inserts as pKD12.138 as well as a pps gene insert encoding for phosphoenolpyruvate (PEP) synthase. PEP synthase catalyzes the conversion of pyruvate back to PEP. Elevated expression of PEP synthase along with transketolase provides an increase in the amount of shikimic acid produced.

In yet another embodiment, the recombinant E. coli comprises plasmid pSC5.112B. This plasmid is derived from and carries the same gene inserts as pKD12.138 as well as a $P_{tac}$glf gene insert encoding for glucose facilitator protein. Elevated expression of the glucose facilitator protein results in an increase in the yield of shikimic acid from the conversion of a carbon source.

In another embodiment, the recombinant microbe employed in the methods of the present invention is E. coli. In a preferred embodiment, the E. coli comprises an aroB cassette inserted into the serA locus and disruption of the aroL and aroK loci (e and f, FIG. 1) and theptsH, ptsI, and crr genes involved in the PTS system of glucose transport. This recombinant E. coli may further comprise an exogenous glucose transport system in place in place of the PTS system. In a preferred embodiment, the recombinant E. coli further comprises a plasmid carrying a glf gene insert. In a more preferred embodiment, the recombinant E. coli further comprises a plasmid carrying both glf and glk gene inserts. The glf gene encodes for a glucose facilitator protein and the glk gene encodes for glucokinase. The glucose facilitator protein provides the host cell with the ability to transport glucose into the cell. In a most preferred embodiment, the glf and glk genes are from Zymononas mobilis. This recombinant E. coli may further comprise a plasmid carrying aroF$^{FBR}$, aroE and serA gene inserts. Shikimic acid accumulates due to the absence of the aroL- and arok-encoded isozymes of shikimate kinase while the second copy of aroB increases the catalytic activity of 3-dehydroquinate synthase. Dell, K.A. et al., J. Am. Chem. Soc. 115:11581 (1993). It w i b e appreciated, however, that the aroL and aroK loci mutations are not essential and are employed to provide greater production of shikimic acid.

In a preferred embodiment, the recombinant E. coli comprises plasmid pSC6.090B. This plasmid is derived from and carries the same gene inserts as pKD12.138 as well as a Ptacglfglk insert encoding for glucose facilitator protein and glucokinase. Elevated expression of the proteins increases the transport and utilization of glucose into the recombinant microbe, thereby increasing the production of shikimic acid. Furthermore, the rate of production of shikimic acid is increased with this construct.

In an alternate preferred embodiment, the recombinant E. coli comprises plasmid pSC6.162A. This plasmid is derived from and carries the same gene inserts as pKD12.138 as well as pps $P_{tac}$ glf gene insert encoding for glucose facilitator protein and PEP synthase.

In another embodiment, the aroF$^{FBR}$, serA, aroE, tkt, pps, glf and/or glk genes are inserted directly into the genome of the host cell. Thus a plasmid would not be required for the production of shikimic acid from such a recombinant microbe.

Examples of the above-described preferred recombinant microbes of the present invention, E. coli SP1.1/pKD12.112, SP2.1/pKD12.112, Sp1.1/pKD12.138, SP2.1/pKD12.138 and SP1.1 pts$^-$/pSC6.090B are described in Specific Example 1 and have been deposited with the American Type Culture Collection (ATCC), P.O. Box 1549, Manassas, Va. 20108, under the terms of the Budapest TTeaty, and accorded the ATCC designation numbers 98905, 98903, 207055, 207054 and PTA-2578, respectively. The deposit will be maintained in the ATCC depository, which is a public depository for a period of 30 years, or 5 years after the most recent request, or for the effective life of a patent, which ever is longer, and will be replaced if the deposit becomes depleted or nonviable during that period. Samples of the deposit will become available to the public and all restrictions imposed on access to the deposit will be removed upon grant of a patent on this application.

The following table sets forth the four enzymes required for the conversion of glucose to shikimic acid, the genes encoding same and the origin of the genes in the exemplary recombinant microbes of the present invention.

TABLE 1

| Enzyme† | Gene (origin) |
| --- | --- |
| a) 3-deoxy-D-arabino-heptulosonic acid 7-phosphate synthase | aroF$^{FBR}$ (plasmid) |
| b) 3-dehydroquinate synthase | aroB (additional copy inserted into genome) |
| c) 3-dehydroquinate dehydratase | aroD (genome) |
| d) 3-dehydroshikimate dehydrogenase | aroE (plasmid) |

†Enzymes a)–d) correspond to a–d of FIG. 1.

Although E. coli is specifically described herein as the microbe for carrying out the methods of the present invention, it will be appreciated that any microorganism such as the common types cited in the literature and known to those skilled in the art, may be employed, provided the microorganism can be altered to effect the desired conversion, e.g., carbon source to shikimic acid. Thus, it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant microbe to form a bioconversion mixture which is maintained under appropriate conditions to promote the conversion of the carbon source to the desired constituent, e.g., shikimic acid. In a preferred embodiment, the bioconversion mixture is maintained at a temperature of about 30° C. to about 37° C. and a pH of about 6.5 to about 7.5. It is preferred that the bioconversion mixture also contain other substances necessary to promote the viability of the recombinant microbes such as mineral salts, buffers, cofactors, nutrient substances and the like. The bioconversion mixture can be maintained under glucose limited conditions or glucose rich conditions. In a preferred embodiment, the rate of glucose addition is determined by the level of dissolved oxygen concentration. A preferred steady state over the course of fermentation is about 100 to about 200 µmol glucose or a dissolved oxygen concentration of about 5% to about 35% air saturation. In an alternate preferred embodiment, glucose rich fermentor conditions are maintained. The glucose concentration is preferably from about 5 g/L to about 50 g/L and more preferably from about 20 g/L to about 25 g/L.

The more general requirements for the maintenance of viability of microorganisms are well known and specific requirements for maintaining the viability of specific microorganisms are also well known as documented in the literature, or are otherwise easily determined by those skilled in the art. The shikimic acid may then be recovered from the bioconversion mixture by methods known in the art (e.g., ion-exchange chromatography) and further purified by recrystallization.

Culturing of the recombinant microbes of the present invention produce not only shikimic acid, but can also produce quinic acid in the fermentation broth. If the quinic acid concentration is too high, it is difficult to purify the shikimic acid away from the quinic acid. In a preferred embodiment, the molar ratio of shikimic acid to quinic acid in the fermentor broth is such that shikimic acid can be purified away from quinic acid. Preferably, the molar ratio will be greater than about 9. More preferably, the molar ratio will be greater than about 20 and most preferably, it will be greater than about 40.

In one embodiment, the molar ratios of shikimic acid to quinic acid in the fermentor broth are controlled by controlling the concentration of the carbon source during fermentation. While not wishing to be bound by theory, it is thought that at lower carbon source concentrations, shikimic acid in the fermentor broth is taken back up by the cells as an alternate carbon source and converted to quinic acid which is then secreted back into the fermentation broth. Increasing the concentration of the carbon source during fermentation inhibits this uptake of shikimic acid and lowers or eliminates the contaminating quinic acid. As a non-limiting example, increasing the glucose concentration by increasing the $K_c$ from 0.1 to 0.8 and thus increasing the rate of addition of a 65% (w/v) glucose solution during fermentation of SP1.1/pKD12.112, resulted in an increase in the molar ratio of shikimic acid to quinic acid from 3.0 to 12.0.

Figure 9:
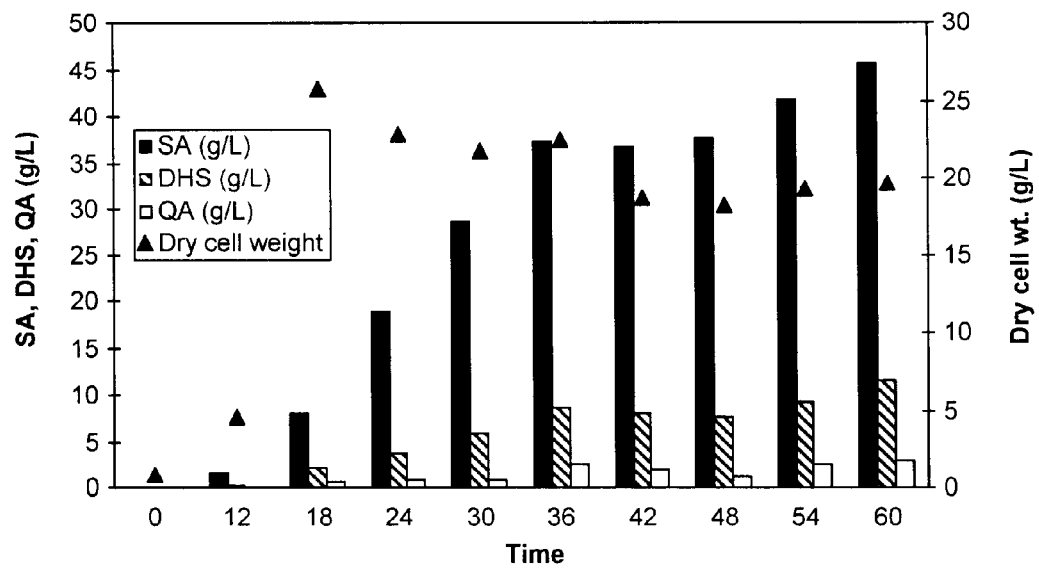
FIG. 9 is a graph showing the production of shikimic acid over time from a carbon source catalyzed by SP1.1/pSC6.090B.

In an alternate embodiment, the molar ratios of shikimic acid to quinic acid in the fermentor broth are controlled by using glucose rich conditions. Glucose rich conditions comprise glucose concentrations preferably from about 5 g/L to about 50 g/L and more preferably, from about 20 g/L to about 25 g/L. As a non-limiting example, the glucose concentration is maintained at 25 g/L during fermentation of PSP1.1 pts⁻/PSC6.090B, resulting in prefered molar ratios of shikimic acid to quinic acid (FIG. 9).

In another embodiment, the molar ratio of shikimic acid to quinic acid is controlled by addition of non-metabolizable (non-hydrolyzable) glucose analogs to the fermentation medium. Preferably, the glucose analog is methyl glucopyranoside present at a concentration of between about 0.1 mM and about 10 mM. More preferably, it is present in a concentration of between about 0.5 and about 1.0 mM. The methyl glucopyranoside may be methyl-α-glucopyranoside, methyl-β-glucopyranoside, or a mixture thereof. Because these analogs are non-hydrolyzable, they may be added only at the beginning of fermentation.

In order to more fully demonstrate the advantages arising from the present invention, the following examples are set forth. It is to be understood that the following is by way of example only and is not intended as a limitation on the scope of the invention.

SPECIFIC EXAMPLE 1

Creation Of Plasmids And Host Strains

Two host strains created for shikimic acid biosynthesis originated from two different *E. coli* strains. *E. coli* SP1.1 was created from RB791, a strain which differs from wild-type W3110 by only a single mutation. A second shikimate-producer, *E. coli* SP2.1, was created from a strain possessing several characterized and an unknown number of uncharacterized mutations. SP2.1 was created from AB2848, an isolate of several rounds of chemical mutagenesis originally selected for a mutation in the dehydroquinate dehydratase-encoding aroD gene. Creation of two organisms for shikimic acid biosynthesis allowed evaluation of the effect of various culture parameters in different genomic backgrounds.

Creation of SP1.1 began with insertion of aroB into the serA locus of RB791 via homologous recombination. This event led to an *E. coli* with increased dehydroquinate synthase expression while inactivating expression of phosphoglycerate dehydrogenase, an enzyme necessary for de novo serine biosynthesis. Subsequent P1-mediated transduction of aroL478::Tn10 and aroK17::Cm$^R$ from *E. coli* AL0807 afforded SP1.1 in which both isozymes of shikimate kinase are inactive. Creation of SP2.1 proceeded similarly but required the additional step of reintroduction of dehydroquinate dehydratase activity to the organism. After insertion of aroB into the serA locus of AB2848, P1-mediated transduction of a functional copy of aroD into the genome afforded an organism capable of aromatic amino acid biosynthesis but not serine biosynthesis. Subsequent P1-mediated transduction of aroL478::Tn10 and aroK17::Cm$^R$ from *E. coli* AL0807 afforded SP2.1.

Construction of EB1.1 followed exactly the same protocols as used for the generation of SP1.1 except that *E. coli* B (ATCC11303) was used as the starting host.

*E. coli* SP1.1 was subjected to P1 phage mediated transduction of (ptsH ptsl crr)::Kn$^R$ thereby knocking out the ptsH, ptsI and crr genes involved in the PTS system of glucose transport. *E. coli* SP1.1 pts⁻was selected based on the following growth characteristics: growth on LB containing Tc. Cm and Km; growth on M9 containing aromatic amino acids, aromatic vitamins and serine only after transformation with plasmid pSC6.090B; no growth on M9 containing aromatic amino acids, aromatic vitamins and serine after transformation with plasmid pSC5.112A and formation of pinkish white colonies on MacConkey agar plates 15 supplemented with 1% glucose.

Plasmid pKD12.112 is a pSU18-based vector (approximately 15 to 20 copies per cell) that contains genes encoding a feedback insensitive isozyme of 3-deoxy-D-arabino-heptulosonate-7-phosphate synthase (aroF$^{FBR}$), shikimate dehydrogenase (aroE), phosphoglycerate dehydrogenase (serA), and β-lactamase (Ap$^R$). Expression of aroF$^{FBR}$, serA, and β-lactamase proceed from their respective native promoters while aroE expression occurs from both its native promoter (designated P$_{aroE}$) and from the strong hybrid promoter tac (P$_{tac}$). Increased expression of a feedback insensitive isozyme of 3-deoxy-D-arabino-heptulosonate-7-phosphate synthase increases the percentage of metabolites directed into shikimate biosynthesis while increased shikimate dehydrogenase expression reduces the impact of this enzyme's inhibition by shikimic acid, thereby reducing byproduct dehydroshikimate formation. Inclusion of serA on pKD12.112 forces host strains SP1.1 and SP2.1 to maintain the plasmid in culture medium lacking serine supplementation. Finally, inclusion of the β-lactamase gene provides additional means of selective pressure for plasmid maintenance in SP1.1 and SP2.1. Resistance to ampicillin, however, was utilized only as a secondary selective pressure during preparation of fermentation inoculants. Ampicillin was never added to fermentation cultures.

Plasmid pKD12.138 was prepared from pKD12.112 by insertion of transketolase-encoding tktA. This 9.9-kb plasmid was created by inserting the 2.2-kb tktA fragment from pMF51A into pKD12.112. Digestion of pMF51A with BamHI followed by treatment with Klenow fragment yielded the tktA gene with blunt ends. Plasmid pKD12.112 was linearized with HindIII and treated with Klenow fragment. Subsequent ligation of the tktA fragment to pKD12.112 resulted in pKD12.138A. The tktA gene is transcribed in the same orientation as the serA gene. Transketolase catalyzes formation of D-erythrose 4-phosphate, an unstable aldose phosphate typically maintained at vanishingly low concentrations in the cell. Elevated expression of transketolase provides additional D-erythrose 4-phosphate for subsequent condensation with phosphoenolpyruvate to form 3-deoxy-D-arabino-heptulosonate-7-phosphate, the first committed intermediate of aromatic amino acid biosynthesis. Increased transketolase expression improves both the rate of formation and the final titer of shikimic acid.

Plasmid pKD15.071B (11.9 kb) was constructed by replacing the 1.0-kb β-lac gene of pKD12.138A by the pps fragment from pKL1.87B. Plasmid pKL1.87B was digested with BamHI and HindIII and the resulting 3.0-kb pps fragment was treated with Klenow fragment. Following digestion of pKD12.138A with NcoI, the 8.9-kb fragment was modified to blunt ends using Klenow fragment. Ligation of these two purified fragments yielded pKD15.071A. The pps gene is transcribed in the opposite orientation relative to the tktA gene.

Plasmid pSC5.112B (11.1 kb) was created by replacing the 1.0-kb -lac gene of pKD12.138A by the glf fragment from pTC325. The 1.9-kb glf gene was excised out of pTC325 along with the 0.3-kb $P_{tac}$ promoter by digestion with BamHI, HindIII and XbaI followed by treatment with Klenow fragment. Plasmid pKD12.138A was digested with NcoI and the 8.9-kb fragment was treated with Klenow fragment. The two purified fragments were ligated to generate pSC5.112B. The $P_{tac}$ glf gene is transcribed in the opposite orientation relative to tktA.

Plasmid pSC6.090B (12.8 kb) was constructed by ligation of the $P_{tac}$ glfglk cassette into pKD12.138. The $P_{tac}$ glfglk cassette was excised out of pTC325 by digestion with BamHI and XbaI followed by treatment with Klenow fragment. Plasmid pKD12.138 was digested with NcoI and the 8.9-kb fragment was treated with Klenow fragment. The two purified fragments were ligated to generate pSC6.090B. The $P_{tac}$ glfglk cassette is transcribed in the same orientation as the tktA gene.

Plasmid pSC 6.142B (7.5 kb) was created by inserting the glf gene into pKL1.87A. Plasmid pTC325 was digested with BamHI, HindIII and XbaI and the resulting 2.2-kb $P_{tac}$ glf fragment was treated with Klenow fragment. Plasmid pKL1.87A was linearized by digestion with SalI followed by treatment with Klenow fragment. Ligation of the $P_{tac}$ glf fragment into pKL1.87A afforded pSC6.142B. The $P_{tac}$ glf gene is transcribed in the opposite orientation relative to the pps gene.

Plasmid pSC6.162A (14.1 kb) was constructed by inserting the 5.2-kb PpsP$_{tac}$ glf cassette from pSC6.142B into pKD12.138. Plasmid pSC6.142B was digested with BamHI and HindIII followed by treatment of the ppsP$_{ta}$ glf fragment with Klenow fragment. The 1.0-kb β-lac gene was excised from the 9.9-kb plasmid pKD12.138A and the remaining 8.9-kb fragment was treated with Klenow fragment. Ligation of the two purified DNA fragments afforded pSC6.162A. The $P_{tac}$ glf fragment was transcribed in the same orientation and the pps gene in the opposite orientation relative to the tktA gene.

SPECIFIC EXAMPLE 2

Synthesis Of Shikimic Acid From Glucose
I. Results

Culturing SP1.1/pKD12.112 for 42 h with $K_c$=0.1 resulted in the synthesis of 27.2 g/L of shikimic acid, 12.6 g/L of quinic acid, and 4.4 g/L of 3-dehydroshikimic acid (DHS). DHS accumulation reflected the expected feedback inhibition of shikimate dehydrogenase by shikimic acid. Draths, K.M. et al., *J. Am. Chem. Soc.* 114:9725 (1992). By contrast, quinic acid biosynthesis was surprising given the absence in E. coli of quinic acid dehydrogenase which catalyzes 3-dehydroquinate and quinic acid interconversion. DHS was readily removed by heating the fermentor broth to convert DHS into protocatechuic acid which was absorbed by activated carbon during decolorization. Unfortunately, quinic acid contamination was in excess of what could be purified away from shikimic acid by crystallization.

Minimizing the cytosolic concentration of 3-dehydroquinic acid appeared to be a reasonable strategy for reducing quinic acid contamination of the shikimic acid synthesized by E. coli SP1.1/pKD12.112. The aroD gene encoding 3-dehydroquinate dehydratase was consequently localized on plasmid pKD12.152A along with aroE, aroF$^{FBR}$ and serA. However, attendant amplified expression of 3-dehydroquinate dehydratase did not reduce the levels of quinic acid contamination in the shikimic acid synthesized by SP1.1/pKD12.152A under fed-batch fermentor conditions identical to those employed for SP1.1/pKD12.112. While not wishing to be bound by theory, these results suggest that quinic acid formation may not result from de novo biosynthesis but rather from equilibration of initially synthesized shikimic acid.

Figure 2:
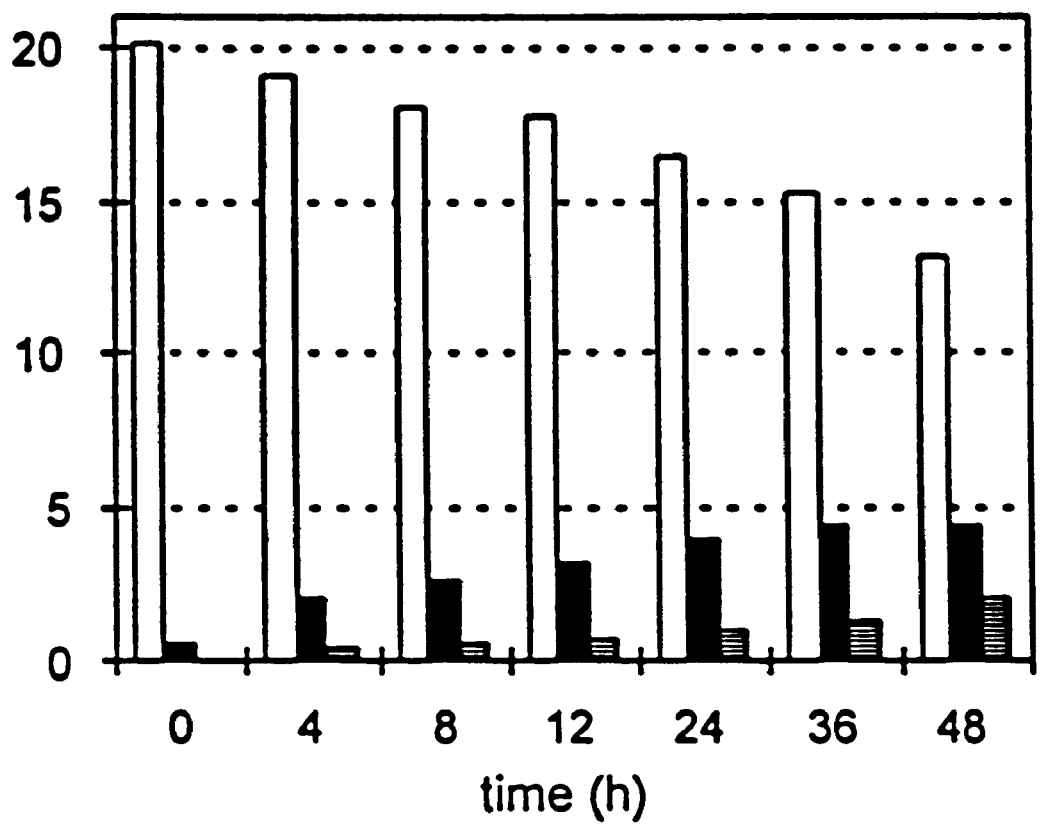
FIG. 2 is a graph showing the equilibrium of shikimic and quinic acids catalyzed by SP1.1/pKD12.112.
Figure 3:
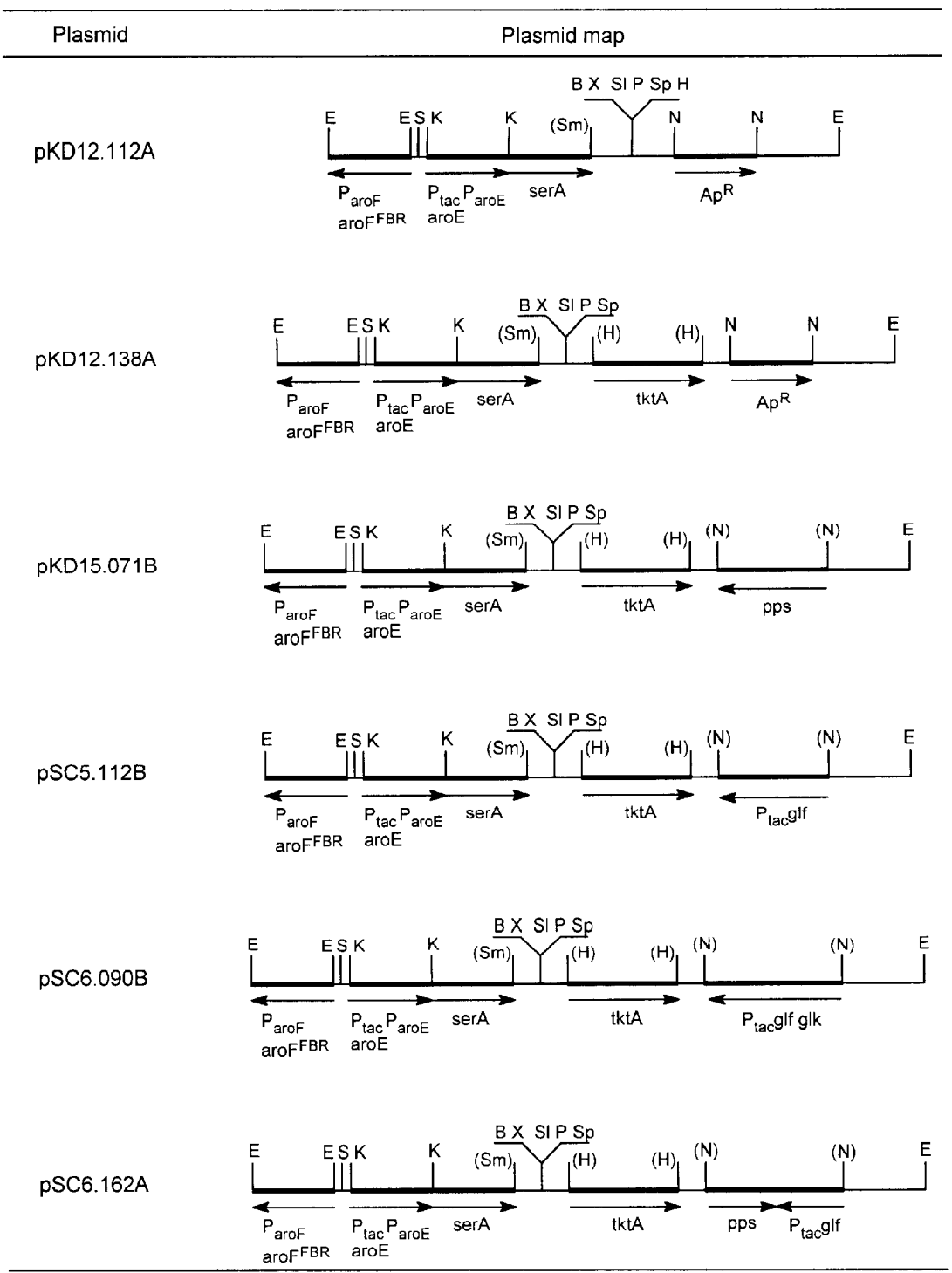
FIG. 3 is a schematic illustrating the plasmid maps of the plasmids of the present invention.
Figure 4:
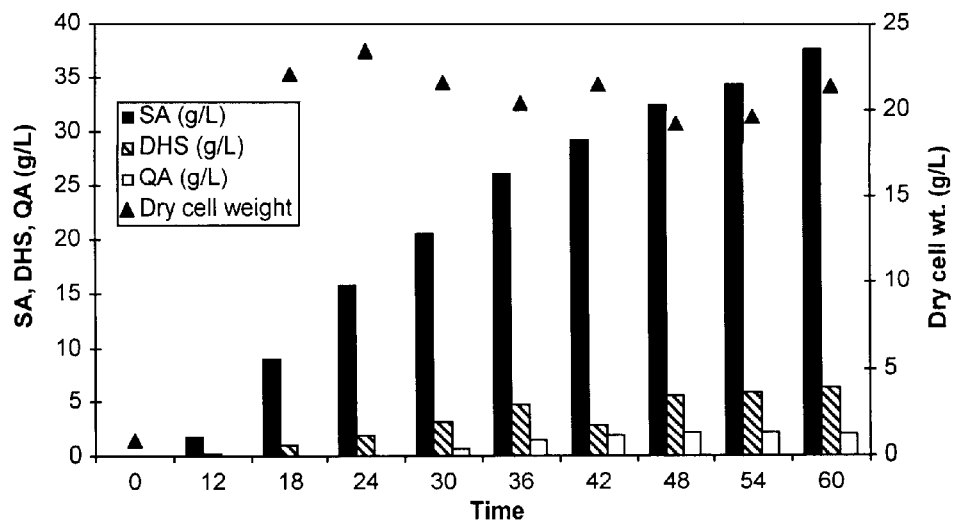
FIG. 4 is a graph showing the production of shikimic acid over time from a carbon source catalyzed by SP1.1/pKD12.112A.
Figure 5:
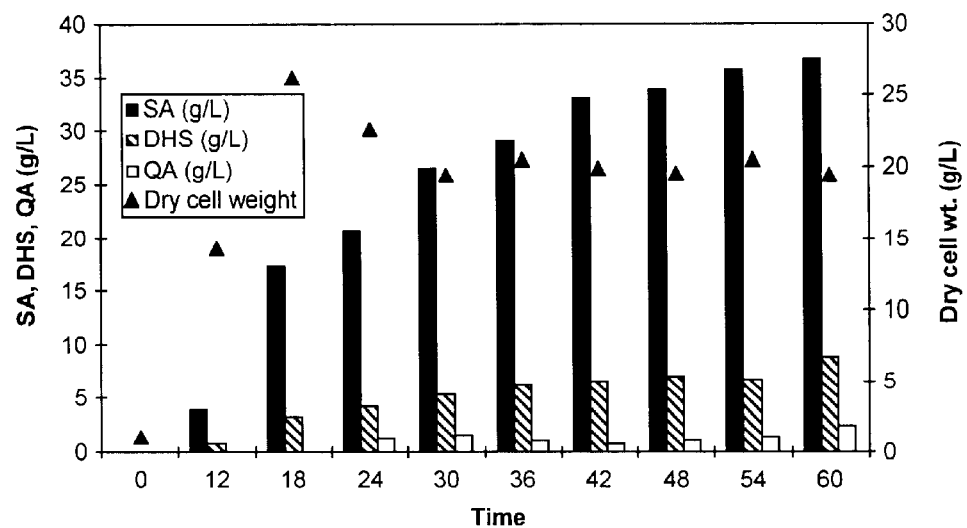
FIG. 5 is a graph showing the production of shikimic acid over time from a carbon source catalyzed by EB1.1/pKD12.138A.

Equilibration of quinic and shikimic acids has previously been examined in cell-free extracts of Klebsiella pneumoniae. Mitsuhashi, S. et al., *Biochim. Biophy. Acta* 15:268 (1954). To be relevant to quinic acid formation in E. coli SP1.1/pKD12.112, the common pathway must be able to operate in vivo in the reverse of its normal biosynthetic direction. To test this possibility, SP1.1/pKD12.112 cells collected from the fermentor after 24 h were washed, resuspended in fresh minimal salts medium containing shikimic acid, and then shaken. Formation of quinic acid (solid bars, FIG. 2) and 3-dehydroshikimic acid (hatched bars, FIG. 2) along with a corresponding decrease in shikimic acid concentration (open bars, FIG. 2) indicated that SP1.1/pKD12.112 can catalyze formation of quinic acid from initially synthesized shikimic acid.

The possible role of shikimic acid transport from the culture medium into the microbial cytoplasm during observed equilibration pointed to a strategy for minimizing quinic acid contamination. Shikimic acid transport (Pittard, J. et al., *J. Bacteriol.* 92:1070 (1966); Brown, K. D. et al., *Biochim. Biophys. Acta* 428:550 (1976)) in E. coli may be an evolutionary vestige of a previous ability to catabolize shikimic and quinic acids as sole sources of carbon for growth and metabolism. Since utilization of non-glucose carbon sources is often subject to catabolite repression, increasing D-glucose availability might repress shikimic acid transport thereby minimizing formation of quinic acid.

The rate of D-glucose addition, and thus D-glucose availability, in all fermentation runs was controlled by the proportional-integral-derivative (PID) setting gain ($K_c$). For example, synthesis by E. coli SP1.1/pKD12.112 of the mixture of shikimic and quinic acids (Table 2) employed a PID setting of $K_c$=0.1. Increasing glucose availability by increasing the PID setting to $K_c$=0.8 resulted (Table 2) in a drastic reduction in the formation of quinic acid throughout the entire fermentation. After 42 h of cultivation, E. coliSP1.1/pKD12.112 synthesized 20.2 g/L of shikimic acid, 4.6 g/L of DHS, and only 1.9 g/L of quinic acid. Under identical conditions SP2.1/pKD12.112 synthesized 37 g/L of shikimic acid, 2.1 g/L of quinic acid and 4.2 g/L of DHS. The decrease in the synthesized titers of shikimic acid is consistent with the known impact of increased D-glucose availability on the concentration and yield of L-phenylalanine synthesized by E coli. Konstantinov, K.B. et al., *J. Ferment Bioeng.* 70:253 (1990); Konstantinov, K.B. et al., *J. Ferment Bioeng.* 71:350 (1991). More importantly, improvement of the shikimate:quinate molar ratio from 2.4:1 ($K_c$=0.1) to 11.8:1 ($K_c$=0.8) allowed quinic acid to be completely removed during crystallization of shikimic acid.

TABLE 2

Products Synthesized By *E. coli* SP1.1/pKD12.112
As A Function Of Time And D-glucose Addition Parameters

|  | $K_c$ = 0.1 | | | $K_c$ = 0.8 | | |
|---|---|---|---|---|---|---|
|  | SA[a] | QA | DHS | SA | QA | DHS |
| 12 h | 1.1 | 0.0 | 0.3 | 1.0 | 0.0 | 0.2 |
| 18 h | 5.3 | 2.5 | 1.2 | 3.1 | 0.0 | 0.6 |
| 24 h | 11.4 | 5.7 | 2.2 | 6.4 | 0.8 | 1.2 |
| 30 h | 17.1 | 8.3 | 2.7 | 10.9 | 1.3 | 2.2 |
| 36 h | 23.1 | 10.8 | 4.2 | 15.7 | 1.8 | 3.5 |
| 42 h | 27.2 | 12.6 | 4.4 | 20.2 | 1.9 | 4.6 |

[a]Concentrations in g/L of shikimic acid (SA), quinic acid (QA), and 3-dehydroshikimic acid (DHS)

Additional fermentation runs resulted in similar yields of shikimic acid and shikimic acid:quinic acid ratios. When the gain ($K_c$) for proportional-integral-derivative control for the glucose feed was set to 0.1, both SP1.1/pKD12.112 and SP2.1/pKD12.112 synthesized less than optimal mixtures of shikimic acid and quinic acid. SP1.1/pKD12.112 achieved a shikimic acid to quinic acid molar ratio of 3.0 while SP2.1/pKD12.112 achieved a molar ratio of 5.0 (Table 3). Attempts to obtain pure shikimic acid from culture broths with molar ratios in this range were unsuccessful. Although synthesis of byproduct DHS represents a loss in shikimic acid titers, DHS is easily separated from shikimic acid during purification. DHS formation was not an obstacle to obtaining pure shikimic acid.

purified away from the quinic acid from culture broths in which the molar ratio exceeds approximately 9.

Although increasing $K_c$ effectively suppresses quinic acid formation, these runs are extremely difficult to control. Dissolved oxygens levels oscillate as a direct result of oscillations in glucose feeding rates. These runs must be closely monitored after approximately 36 h into the run in order to avoid large, unnecessary additions of glucose. Since the runs could routinely be nursed along through 42 h but rarely through 48 h without a loss of control, the runs were terminated after 42 h. Increasing the steady-state glucose concentration in the culture broth also had a significant impact on the rate of shikimic acid production for SP1.1/pKD12.112. At the higher gain, SP1.1/pKD12.112 synthesized 20.2 g/L of shikimic acid after 42 h, as compared to 33 g/L at this same time when the gain was set to the lower value. The effect on the rate of production, however, was not observed for SP2.1/pKD12.112.

An alternative to increasing $K_c$ in order to suppress quinic acid formation was addition of a non-hydrolyzable glucose analog to the fermentation broth. Methyl $\alpha$-D-glucopyranoside ($M_\alpha DG$) was added to the fermentation medium at the time of inoculation and the fermentation was then run without further adjustment. Addition of 1 mM $M_\alpha DG$ to the fermentation of SP1.1/pKD12.112 resulted in the synthesis of 40.3 g/L of shikimic acid (Table 3). Quinic acid was not detected. Although several concentrations were examined, 1 mM $M_\alpha DG$ was the minimum concentration that afforded complete suppression of quinic acid formation. Addition of $M_\alpha DG$ to SP2.1/pKD12.112 cultures also resulted in quinic acid suppression. After 48 h of culturing in the presence of 0.5 mM $M_\alpha DG$, SP2.1/pKD12.112 (Table 3) synthesized 39.6 g/L of shikimic acid and 4.1 g/L of quinic acid, resulting in a molar ratio 11. Higher concentrations of $M_\alpha DG$ showed no further improvement in quinic acid suppression.

With conditions established that adequately suppress quinic acid formation without significantly compromising

TABLE 3

Summary Of Fermentation Results

| Strain | Modification | $K_c$ | SA[a] (g/L) | QA[a] (g/L) | DHS[a] (g/L) | Molar Ratio SA:QA |
|---|---|---|---|---|---|---|
| SP1.1/pKD12.112 | — | 0.1 | 38.2 | 12.4 | 6.5 | 3.0 |
| SP2.1/pKD12.112 | — | 0.1 | 33.2 | 7.8 | 5.4 | 5.0 |
| SP1.1/pKD12.112 | increase $K_c$ | 0.8 | 20.2[b] | 1.9 | 4.6 | 12 |
| SP2.1/pKD12.112 | increase $K_c$ | 0.8 | 36.6[b] | 2.2 | 4.4 | 18 |
| SP1.1/pKD12.112 | add M $\alpha$DG (1 mM) | 0.1 | 40.3 | 0 | 5.3 | >40 |
| SP2.1/pKD12.112 | add M $\alpha$DG (0.5 mM) | 0.1 | 39.6 | 4.1 | 4.8 | 11 |
| SP1.1/pKD12.138 | add M $\alpha$DG (1 mM); tktA | 0.1 | 51.1 | 4.3 | 8.8 | 13 |
| SP2.1/pKD12.138 | add M $\alpha$DG (0.5 mM); tktA | 0.1 | did not change phase | | | |

[a]after 48 h of culturing except as noted differently
[b]after 42 h of culturing When the gain controlling the glucose feed was increased from 0.1 to 0.8, significant improvement in the shikimic acid to quinic acid molar ratio was observed. Increasing $K_c$ to 0.8 results in a stronger response by the glucose pump when the dissolved oxygen level deviates from its setpoint. Increased values of $K_c$ therefore result in higher steady-state glucose concentrations in the culture medium. After 42 h of culturing with $K_c$ set at 0.8, SP1.1/pKD12.112 synthesized 20.2 g/L of shikimic acid and only 1.9 g/L of quinic acid to achieve a molar ratio of 12 (Table 3). Comparable improvement was seen with SP2.1/pKD12.112 which achieved a molar ratio of 18 by synthesizing 36.6 g/L of shikimic acid and 2.2 g/L of quinic acid after 42 h (Table 3). Shikimic acid readily control, attention was turned to increasing shikimic acid titers using transketolase overexpression. When cultured in the presence of 1 mM $M_\alpha DG$, SP1.1/pKD12.138 synthesized 51.1 g/L of shikimic acid and 4.3 g/L of quinic acid, affording a molar ratio exceeding 13 (Table 3). Transketolase expression resulted in a 25% increase in shikimic acid titers while maintaining a molar ratio of shikimic acid to quinic acid that allows shikimic acid isolation. The concentration of DHS byproduct also increased to 8.8 g/L, providing added incentive to obtain a shikimate dehydrogenase insensitive to shikimic acid inhibition. When SP2.1/pKD12.138 was cultured under standard conditions, the fermentation never reached the point of phase change. At 33° C. growth of SP2.1/pKD12.138 was slow and resulted in significant acetate production.

Increases in shikimic acid production were obtained by manipulating the transport and utilization of glucose in the cell. One limiting step to shikimic acid production is the amounts PEP is available to the cell. Conversion of pyruvic acid into PEP is catalyzed by pps-encoded PEP synthetase, which expends two phosphodiester bonds of ATP to convert pyruvic acid into PEP. Although pps is a chromosomal locus in wild-type *E. coli*, the regulation of this enzyme's transcription and in vivo catalytic activity has not been elaborated. Liao and coworkers were the first to report that overexpressed pps resulted in substantial increases in carbon flow directed into the common pathway of aromatic amino acid biosynthesis. U.S. Pat. No. 5,906,925; Patnaik, R. et al., *Appll. Environ. Microbiol.* 60, 3903 (1994).

Figure 6:
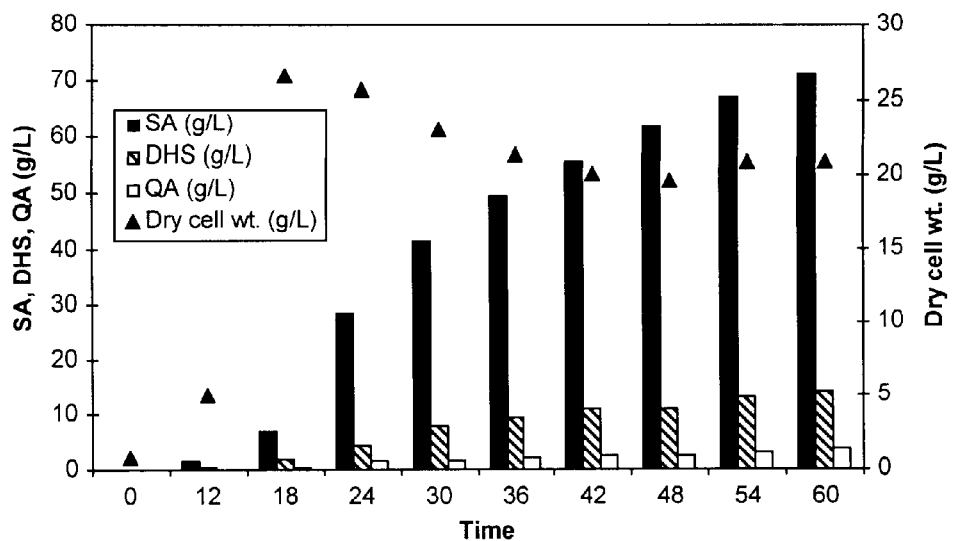
FIG. 6 is a graph showing the production of shikimic acid over time from a carbon source catalyzed by SP1.1/pKD15.071B.
Figure 7:
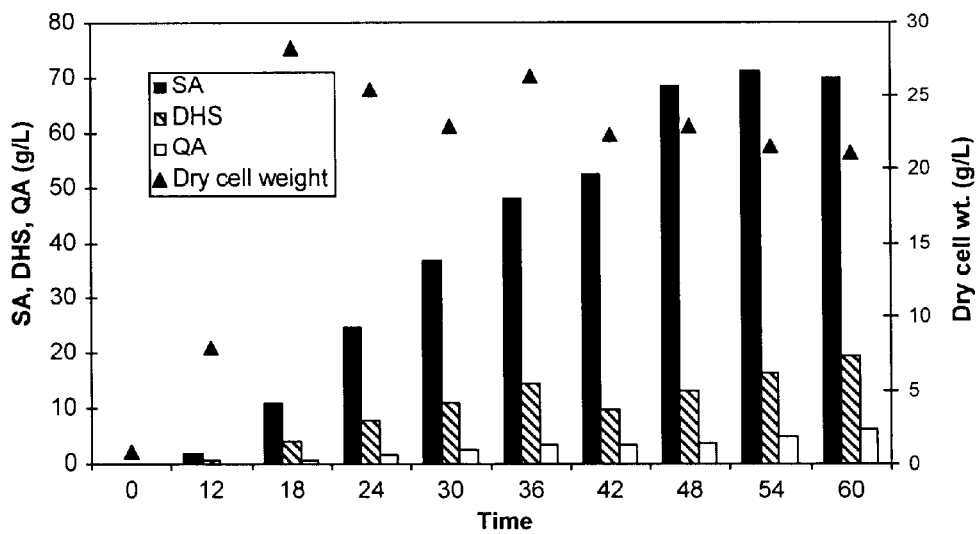
FIG. 7 is a graph showing the production of shikimic acid over time from a carbon source catalyzed by SP1.1/pSC5.112B.
Figure 8:
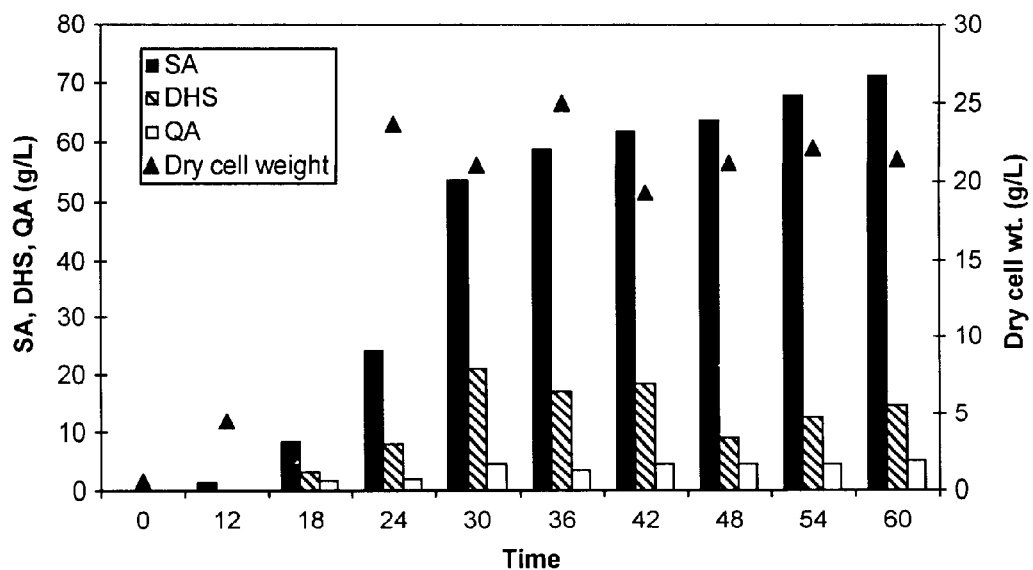
FIG. 8 is a graph showing the production of shikimic acid over time from a carbon source catalyzed by SP1.1 ptsipSC6.090B.

PPS-overexpressing SP1.1/pKD15.071B synthesized (entry 3, Table 4; FIG. 6) 66 g/L of shikimic acid in 23% yield from glucose under glucose rich fermentor conditions which compares with 52 g/l of shikimic acid synthesized in 18% yield by SP1.1/pKD12.138A (entry 2, Table 4; FIG. 7). SP1.1/pKD12.138 is most appropriate for comparison with SP1.1/pKD15.071B since both constructs employ plasmid localized tktA. Overexpression of tktA-encoded transketolase is essential for increased carbon flow directed into aromatic amino acid biosynthesis to be realized upon overexpression of pps-encoded PEP synthetase.[2a] Patnaik, R. et al., *Appl. Environ. Microbiol.* 60, 3903 (1994).

SP1.1/pSC6.090B and SP1.1/pSC6.162A. SP1.1/pSC6.090B retained the PTS system but carried plasimid-localized glf and glk. SP1.1/pSC6.162 also retained the PTS system and carried plasmid localized glf but was additionally equipped with plasmid-localized pps for recycling of PTS-generated pyruvic acid back to PEP. Keeping the PTS system operational while equipping the construct with facilitated glucose transport was employed in SP1.1/pSC5.112B and SP1.1/pSC6.090B due to concerns of what impact inactivating the PTS system would have on the growth and metabolic vigor of E. col. This was a particular concern given the high density conditions employed in the microbial syntheses of shikimic acid under fed-batch fermentor conditions. Along these lines, the final variant is SP1.1pts⁻pSC6.090B, which had PTS-mediated glucose transport inactivated and is completely dependent on the glf-encoded facilitator and glk-encoded kinase for glucose transport and phosphorylation.

Figure 10:
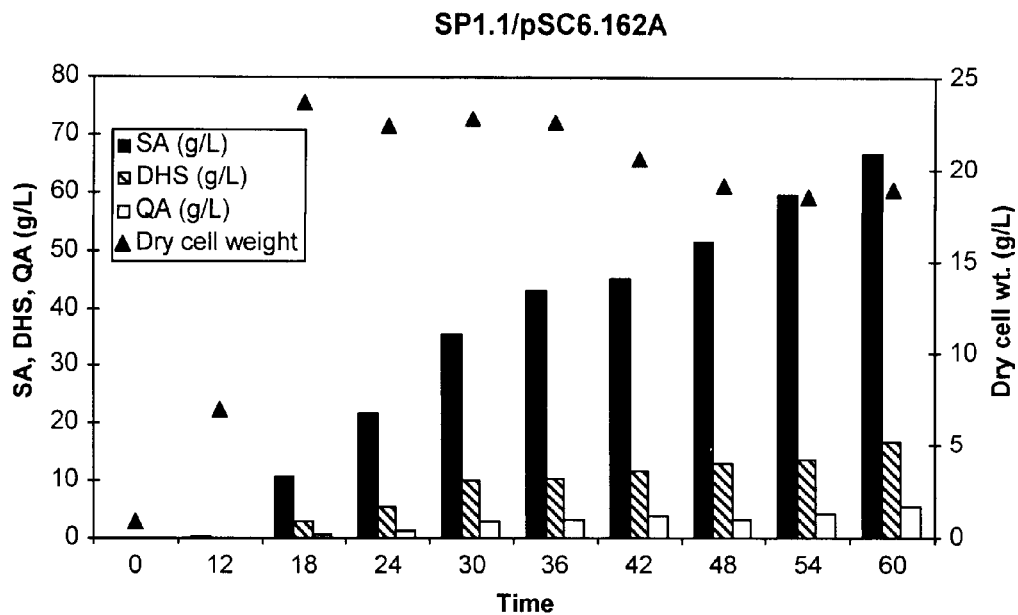
FIG. 10 is a graph showing the production of shikimic acid over time from a carbon source catalyzed by SP1.1/pSC6.162A.

The highest yield (27%) and the highest titer (71 g/L) of shikimic acid was synthesized (entry 5, Table 4; FIG. 10) by SP1.1pts⁻/pSC6.090B under glucose rich fermentation conditions. This construct synthesed shikimic acid at the fastest rates observed for any shikimate-producer. SP1.1pts-IpSC6.090B synthesized 54 g/L of shikimic acid within 30 h (FIG. 10). From 24 h to 30 h, SP1.1pts⁻/pSC6.090B synthesized shikimic acid at a productivity of 5 g/L/h. SP1.1/pSC5.112B, which was capable of glucose transport by both PTS and Glf but lacked Glk, was also a good

TABLE 4

| Entry no. | Strain | [SA] (g/L) | SA yield (mol/mol) | [DHS] (g/L) | [QA] (g/L) | Total yield (mol/mol) |
| --- | --- | --- | --- | --- | --- | --- |
| 1 | SP1.1/pKD12.112 | 38 | 12% | 6 | 2 | 15% |
| 2 | SP1.1/pKD12.138 | 52 | 18% | 11 | 4 | 24% |
| 3 | SP1.1/pKD15.071B | 66 | 23% | 16 | 4 | 29% |
| 4 | SP1.1/pSC5.112B | 70 | 24% | 19 | 6 | 32% |
| 5 | SP1.1pts⁻/pSC6.090B | 71 | 27% | 15 | 5 | 34% |
| 6 | SP1.1/pSC6.090B | 46 | 21% | 16 | 3 | 28% |
| 7 | SP1.1/pSC6.162A | 67 | 26% | 17 | 5 | 34% |
| 8 | EB1.1/pKD12.112A | 39 | 17% | 8 | 2 | 21% |
| 9 | EB1.1/pKD12.138A | 37 | 22% | 9 | 2 | 28% |
| 10 | EB1.1/pKD15.071B | 44 | 18% | 10 | 2 | 22% |

Equipping shikimate-synthesizing *E. coli* with the glf-encoded glucose facilitator cloned out of *Zymononas mobilis* provides an opportunity to prevent loss of three carbon atoms for the transport of every six (glucose) carbon atoms by eliminating exclusive reliance on PTS-mediated glucose transport. The glf-encoded glucose facilitator does not require PEP expenditure, but typically requires a concentration gradient to drive transport into the microbial cytoplasm. This is not problematic since shikimic acid synthesis using *E. coli* K12 is best performed using an excess of glucose in the culture medium to prevent unwanted equilibration of shikimic acid with quinic acid. Draths, K. M. et al., *J. Am. Chem. Soc.* 121, 1603 (1999).

Figure 11:
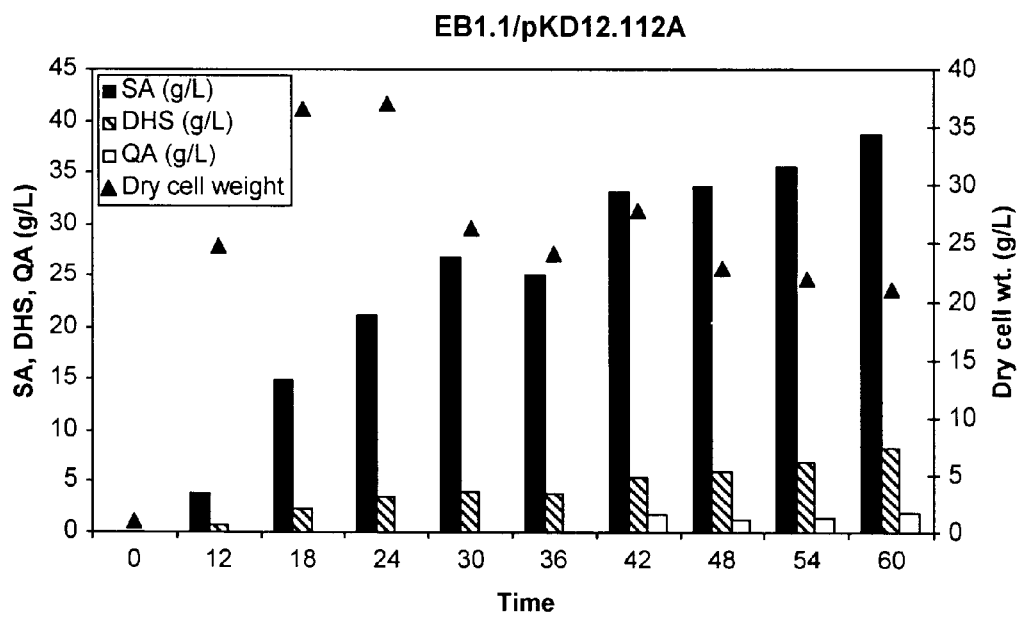
FIG. 11 is a graph showing the production of shikimic acid over time from a carbon source catalyzed by EB1.1/pKD12.112A.
Figure 12:
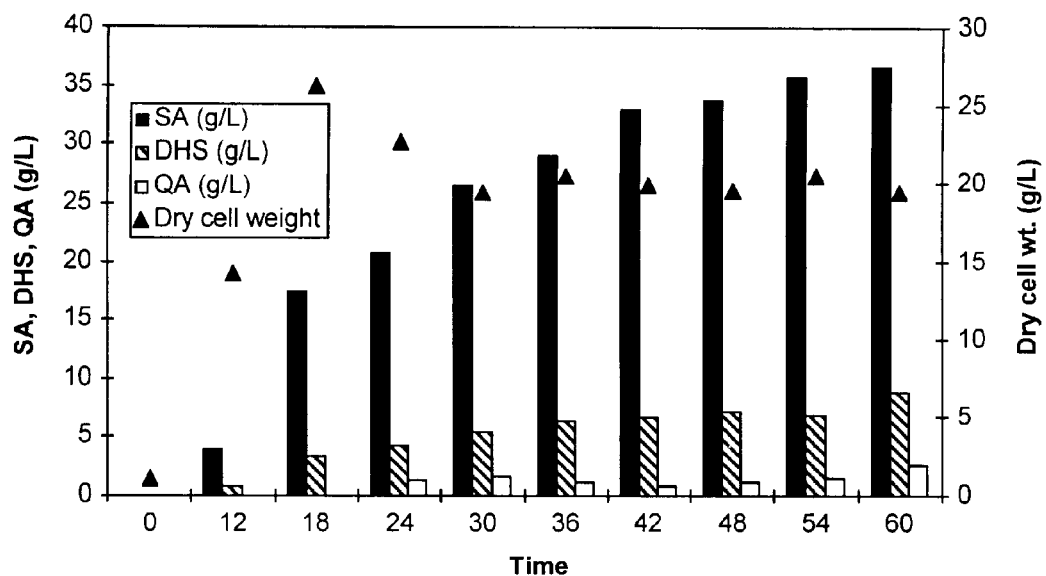
FIG. 12 is a graph showing the production of shikimic acid over time from a carbon source catalyzed by EB1.1/pKD12.138A.
Figure 13:
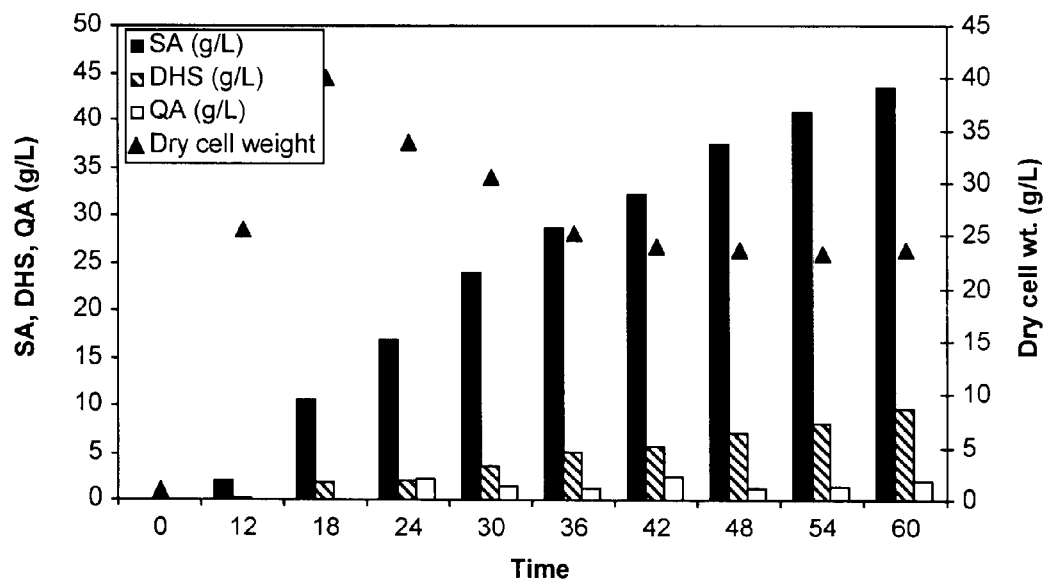
FIG. 13 is a graph showing the production of shikimic acid over time from a carbon source catalyzed by EB1.1/pKD15.071B.

Three permutations were explored for glf-mediated glucose transport. *E. coli* SP1.1/pSC5.112B retained the phosphoenolpyruvate carbohydrate phosphotransferase (PTS) system for glucose transport but was also equipped with the glf-encoded glucose facilitator. No glk-encoded glucose kinase was included in SP1.1/pSC5.112B since this construct was not completely dependent on the facilitator for glucose transport. It was thought that native glucokinase activity was sufficient for phosphorylation of the glucose transported by Glf. Other variations on this approach were shikimate-producing construct (entry 4, Table 4; FIG. 9) with 70 g/L of shikimic acid synthesized in 24% yield under the same conditions. However, SP1.1/pSC5.112B did not produce shikimic acid as rapidly as SP1.1pts⁻/pSC6.090B. The expression of both glf and glk along with retention of PTS-mediated glucose transport in SP1.1/pSC6.090B resulted in a significant reduction in the titers (46 g/L) of synthesized shikimic acid (entry 6, Table 4; FIG. 11). The attempt with SP1.1/pSC6.162 to combine the glf and pps strategies in one construct did not result in an improvement in shikimic acid titers or yields (entry 7, Table 4, FIG. 12) relative to what was observed for SP1.1/pSC5.112B (PTS with Glf) or SP1.1/pKD15.071B (PTS with Pps).

Another strategy to increase the synthesized titers and yields of shikimic acid is to explore use of a different microbe. Constructing a shikimate-synthesizing *E. coli* B construct allows the advantage that many of the cloning techniques used to construct the shikimate-synthesizing *E. coli* K12 constructs could be used. Geneticists have historically favored *E. coli* K12 while *E. coli* B was favored by physiologists due to its more rapid growth relative to *E. coli* K12 in minimal medium. Draths, K. M. et al., *J. Am. Chem. Soc.* 121, 1603 (1999). *E. coli* B is also naturally deficient in a number of proteases that may be responsible for the decline in AroF$^{FBR}$ activity that is often observed during stationary phase. Ongoing commercialization of ethanologenic *E. coli* B constructs for production of ethanol from neutralized hydrosylate of sugar cane bagasse suggests that *E. coli* B may be quite resilient towards osmotic stress associated with synthesis of high concentrations of shikimic acid. Flores, N. et al., *Nature Biotechnology*, 620, 1996 (1996).

*E. coli* B construct EB1.1/pKD12.112A had higher DAHP synthase specific activities (Table 5) relative to the parallel *E. coli* K12 construct SP1.1 pKD 2.112A under glucose rich fermentation conditions. Similarly, EB1.1/pKD12.138 had higher DAHP synthase specific activities (Table 5) relative to the parallel *E. coli* K12 construct SP1.1/pKD12.138. However, DAHP specific activities were not any more stable over time for the *E. coli* B constructs (entry 1 and 2, Table 4) relative to the *E. coli* K12 constructs (entry 3 and 4, Table 5). Transketolase specific activities were substantially higher for the *E. coli* B constructs relative to the corresponding parallel *E. coli* K12 constructs (entry 5 vs. entry 7, entry 6 vs entry 8, Table 5).

TABLE 5

| Entry no. | Strain | 12 h | 24 h | 36 h | 48 h |
|---|---|---|---|---|---|
| | | DAHP synthase specific activities | | | |
| 1 | EB1.1/pKD12.112A | 1.51 | 1.13 | 0.99 | 0.84 |
| 2 | EB1.1/pKD12.138A | 0.82 | 0.80 | 0.49 | 0.41 |
| 3 | SP1.1/pKD12.112A | 0.37 | 0.35 | 0.37 | 0.31 |
| 4 | SP1.1/pKD12.138A | 0.068 | 0.192 | 0.128 | 0.096 |
| | | Transketolase specific activities | | | |
| 5 | EB1.1/pKD12.112A | 0.073 | 0.17 | 0.34 | 0.39 |
| 6 | EB1.1/pKD12.138A | 0.11 | 0.50 | 0.73 | 0.53 |
| 7 | SP1.1/pKD12.112A | 0.024 | 0.10 | 0.14 | 0.18 |
| 8 | SP1.1/pKD12.138A | 0.11 | 0.17 | 0.21 | 0.35 | specific activities are in units/mg; 1 unit = 1 μmol/min

Despite the higher specific activities of DAHP synthase and transketolase, EB 1.1/pKD2.112 (entry 8, Table 4) synthesized approximately the same titers (39 g/L) of shikimic acid albeit at a higher yield (17%) relative to SP1.1/pKD12.112 A (entry 1, Table 4). Neither plasmid localization of tktA in EB1.1/pKD12.138A (entry 9, Table 4) or plasmid localization of pps in EB1.1 /pKD15.071B (entry 10, Table 4) improved both the titer and yield of synthesized shikimic acid relative to EB 1.1/pKD12.112 (entry 8, Table 4).

Microbial synthesis of shikimic acid as described in the present invention can supplant isolation of this hydroaromatic from plant sources which has limited shikimic acid's synthetic utility. At the same time, increased availability of shikimic acid will portend wider utilization of this hydroaromatic. The theoretical maximum yield for microbial synthesis of shikimic acid is 43% from D-glucose. Draths, K.M. et al., *J. Am. Chem. Soc.* 117:2395 (1995). Comparison with the yields achieved thus far for microbial synthesis of shikimic acid (14–22%) along with the apparent lack of toxicity of this hydroaromatic toward the microbial biocatalyst suggest that sizable increases in yields and titers are possible. Such improvements coupled with economies of scale associated with large scale fermentation can even extend utilization of shikimic acid from chiral synthon to disposable chirality employable in the manufacture of large-volume aromatic chemicals.

II. Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP (δ=0.00 ppm) in the $^1$H NMR. All $^1$H NMR spectra were recorded on a Varian VXR-300 FT-NMR Spectrometer (300 MHz).

Culture Medium. All medium was prepared in distilled, deionized water. M9 salts (1 L) contained $Na_2HPO_4$ (6 g), $KH_2PO_4$ (3 g), NaCl (0.5 g) and $NH_4Cl$ (1 g). M9 minimal medium (1 L) consisted of 1 L of M9 salts containing D-glucose (10 g), $MgSO_4$ (0.12 g), thiamine hydrochloride (0.001 g), L-phenylalanine (0.040 g), L-tyrosine (0.040 g), L-tryptophan (0.040 g), p-hydroxybenzoic acid (0.010 g), potassium p-aminobenzoate (0.010 g), and 2,3-dihydroxybenzoic acid (0.010 g). Ampicillin was added (0.05 g/L) where indicated. Solutions of M9 salts, $MgSO_4$, and glucose were autoclaved individually and then mixed. Aromatic amino acids, aromatic vitamins, and ampicillin were sterilized through 0.22-μm membranes.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (20 g), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24})$ 5.4$H_2O$ (0.0037 g), $ZnSO_4$.7$H_2O$ (0.0029 g), $H_3BO_3$ (0.0247 g), $CuSO_4$.5$H_2O$ (0.0025 g), and $MnCl_2$.4$H_2O$ (0.0158 g). D-Glucose and $MgSO_4$ were autoclaved separately while aromatic vitamins and trace minerals were sterilized through 0.22-μm membranes.

Fermentations Under Glucose Limited Conditions. Fermentations employed a 2.0 L working capacity B. Braun M2 culture vessel. Utilities were supplied by a B. Braun Biostat MD that was controlled by a DCU-1. Data acquisition utilized a Dell Optiplex Gs$^+$5166M personal computer equipped with B. Braun MFCS/Win software. Temperature, pH, and glucose feeding were controlled with PID control loops. Temperature was maintained at 33° C. pH was maintained at 7.0 by addition of concentrated $NH_4OH$ or 2 N $H_2SO_4$. Dissolved oxygen (D.O.) was measured using a Mettler-Toledo 12 mm sterilizable $O_2$ sensor filted with an Ingold A-type $O_2$ permeable membrane. D.O. was maintained at 10% air saturation.

Inoculants were started by introduction of a single colony into 5 mL of M9 medium containing ampicillin. The culture was grown at 37° C. with agitation at 250 rpm for 24 h and subsequently transferred to 100 mL of M9 medium containing ampicillin. After growth at 37° C., 250 rpm for an additional 12 h, the inoculant was ready for transfer into the fermentation vessel. The initial glucose concentration in the fermentation medium was 20 g/L. Three staged methods were used to maintain D.O. levels at 10% air saturation during the course of run. With the airflow at an initial setting of 0.06 L/L/min, D.O. concentration was maintained by increasing the impeller speed from its initial set point of 50 rpm to its preset maximum of 940 rpm. With the impeller constant at 940 rpm, the mass flow controller then maintained D.O. levels by increasing the airflow rate from 0.06 L/L/min to a preset maximum of 1.0 L/L/min. At constant impeller speed and constant airflow rate, D.O. levels were finally maintained at 10% air saturation for the remainder of the fermentation by oxygen sensor-controlled glucose feeding. At the beginning of this stage, D.O. levels fell below 10% air saturation due to residual initial glucose in the medium. This lasted for approximately 1 h before glucose (65% w/v) feeding started. The PID control parameters were set to 0.0 (off) for the derivative control ($_{\tau D}$) and 999.9 s (minimum control action) for integral control ($_{\tau I}$). $X_p$ was set to 950% to achieve a $K_c$ of 0.1 and 125% to achieve a $K_c$ of 0.8.

Fed-Batch Fermentation Under Glucose Rich Conditions. Fed-batch cultures were performed in a 2.0 L capacity Biostat MD B-Braun fermentor connected to a DCU system and a Dell Optiplex Gs+5166M personal computer loaded with B-Braun MFCS/win software for data acquisition and automatic process monitoring. The temperature, pH and dissolved oxygen (D.O.) were controlled with PID control loops. The temperature was maintained at 33° C., D.O. at 10% and the pH was kept steady at 7.0 by addition of either concentrated $NH_4OH$ or 2N $H_2SO_4$. D.O. levels were monitored using a Mettler-Toledo 12 mm sterilizable $O_2$ sensor fitted with an Ingold A-type permeable membrane.

A typical inoculant was started by introduction of a single colony of the strain under investigation into 5 mL of complete M9 medium. This starter culture was grown with agitation at 250 rpm for 24 h at 37° C. The culture was then transferred to 100 mL of complete M9 medium and grown for an additional 10 h at 37° C. and 250 rpm before being transferred to the fermentor containing 1.0 L of fermentation medium. The fermentation can be divided into three distinct stages based on the method used to maintain the D.O. at 10%. In the first stage, with the air flow set at 0.06 L/L/min, the impeller speed ramped up from 50 rpm to 750 rpm. Once the maximum impeller speed was attained, the mass flow controller maintained the D.O. level at 10% by increasing the airflow from 0.06 L/L/min to 1.0 L/L/min. Once the air flow rate levelled off at 1.0 L/L/min at a constant impeller speed of 750 rpm, glucose was manually pumped into the fermentor so as to maintain an average glucose concentration of 25 g/L throughout the run. At this stage, the D.O. level was maintained at 10% by allowing the impeller speed to vary from 750 rpm tp 1600 rpm. Fermentations were typically run for 60 h.

Analysis of Fermentation broth. During the course of the fermentation, 5 mL aliquots were removed every 6 h starting at 12 h into the run. Cell densities were determined by measurement of absorbance at 600 nm ($OD_{600}$) Dry cell weight (g/L) was calculated using a conversion factor of 0.43 g/L/$OD_{600}$. The fermentation sample was centrifuged using a Beckman microfuge. A portion (0.5–1.0 mL) of the supernatant was concentrated to dryness under reduced pressure, treated with 1.0 mL of $D_2O$ and again concentrated to dryness. The residue obtained was dissolved in 1.0 mL $D_2O$ containing 10 mM of the internal standard, sodium salt of 3-(trimethylsilyl)propionic-2,2,3,3-$d_4$ acid (TSP, =0.00 ppm), purchased from Lancaster Synthesis Inc. Concentrations of metabolites in the culture supernatant were determined by comparison of integral values corresponding to each metabolite in the $^1H$ NMR spectra with the integral corresponding to TSP. All $^1H$ NMR spectra were recorded on a Varian VXR-300 FT-NMR spectrometer (300 MHz).

Purification of Shikimic Acid from Fermentation Broth. The fermentation broth (1100–1200 mL) was centrifuged at 14000g for 20 min and the cells were 5 discarded. The resulting supernatant was refluxed for 4 h, cooled to room temperature, and the pH adjusted to 2.5 by addition of concentrated $H_2SO_4$. After centrifugation at 14000 g for 20 min, a clear yellow solution was poured away from the cellular debris and adjusted to pH 6.9 by addition of concentrated $NH_4OH$. The solution was combined with 5 g of Darco KB-B activated carbon, swirled at 50 rpm for 1–2 h, and then filtered through Whatman 5 filter paper. Filtered material was washed with an additional 250 mL of water. The combined filtrates were then treated in the same way with a second batch of activated carbon.

Following treatment of the solution with carbon, the dark color was less intense than prior to treatment, but the solution was not colorless. Addition of glacial acetic acid to a final concentration of 15% afforded a clear, yellow solution which was then eluted through a column of AG1-x8 (acetate form, 5 cm×20 cm) at 4° C. Following elution of the column with an additional 400 mL of 15% aqueous acetic acid, the combined eluents were passed through a column of Dowex 50 ($H^+$form, 5 cm×20 cm) at 4° C. which was then washed with 400 mL of 15% aqueous acetic acid. The eluents off the cation exchange column were combined and concentrated to approximately 150 mL by boiling and then to dryness by rotary evaporation, leaving a hard white solid (83% recovery through this step). Recrystallization from a mixture of methanol and ethyl acetate afforded shikimic acid as a fine white powder (61% recovery based on shikimic acid quantified in crude fermentation broth).

The foregoing discussion discloses and describes merely exemplary embodiments of the present invention. One skilled in the art will readily recognize from such discussion, and from the accompanying drawing and claims, that various changes, modifications and variations can be made therein without departing from the spirit and scope of the invention as defined in the following claims.

All references cited herein are incorporated by reference as if fully set forth. In addition, U.S. Ser. No. 09/240,441, entitled "Biocatalytic Synthesis Of Quinic Acid," filed Jan. 29, 1999, is also expressly incorporated by reference.

We claim:

1. A method for the production of shikimic acid from a carbon source comprising:
   a) providing a microbe selected from the group consisting of bacteria and fungi including yeast, wherein the microbe comprises one or more enzyme-encoding recombinant DNA molecules, wherein the encoded enzyme is selected from the group consisting of 3-deoxy-D-arabino-heptulosonic acid 7-phosphate synthase, 3-dehydroquinate synthase, 3-dehydroquinate dehydratase, and 3-dehydroshikimate dehydrogenase, and wherein the microbe further comprises an inactivating mutation of at least one DNA molecule which encodes a shikimate kinase isozyme, and wherein the microbe further comprises an inactivating mutation in at least one DNA sequence which encodes a gene involved in the phosphoenolpyruvate carbohydrate phosphotransferase system; and
   b) culturing the microbe in the presence of the carbon source; and
   c) isolating the shikimic acid produced.

2. The method of claim 1, wherein the microbe is an *E. coli*.

3. The method of claim 1, wherein the recombinant DNA sequence encoding 3-dehydroshikimate dehydrogenase is a recombinant aroE.

4. The method of claim 1, wherein the recombinant DNA sequence encoding 3-dehydroquinate synthase is a recombinant aroB.

5. The method of claim 1, wherein the inactivating mutation or deletion of at least one DNA sequence which encodes a shikimate kinase isozyme produces an elimination or reduction in shikimate kinase activity.

6. The method of claim 1, wherein the inactivating mutation or deletion of at least one DNA sequence which encodes a shikimate kinase isozyme is a deletion mutation in either or both of an aroK and an aroL gene.

7. The method of claim 1, wherein the microbe further comprises a recombinant DNA sequence encoding a glucose transport facilitator protein.

8. The method of claim 7, wherein the recombinant DNA sequence encoding a glucose transport facilitator protein comprises a glf sequence.

9. The method of claim 8, wherein the glf sequence is from *Zymononas mobilis*.

10. The method of claim 1, wherein the microbe further comprises a recombinant DNA sequence encoding a glucose kinase.

11. The method of claim 10, wherein the recombinant DNA sequence encoding a glucose kinase comprises a glk sequence.

12. The method of claim 11, wherein the glk sequence is from *Zymononas mobilis*.

13. The method of claim 1, wherein the recombinant DNA sequence encoding 3-deoxy-D-arabino-heptulosonic acid 7-phosphate synthase encodes a 3-deoxy-D-arabino-heptulosonic acid 7-phosphate synthase insensitive to feedback inhibition, thereby increasing the flow of carbon from the carbon source into the common aromatic amino acid biosynthetic pathway of the microbe.

14. The method of claim 13, wherein the recombinant DNA sequence encoding 3-deoxy-D-arabino-heptulosonic acid 7-phosphate synthase insensitive to feedback inhibition is a recombinant aroF$^{FBR}$.

15. The method of claim 1, wherein the recombinant DNA sequence encoding 3-dehydroquinate dehydratase is a recombinant aroD.

16. The method of claim 1, wherein culturing the cell in the presence of the carbon source further comprises culturing the cell in the presence of an excess amount of the carbon source.

17. The method of claim 16, wherein the excess amount of the carbon source produces a molar ratio of shikimic acid to quinic acid which is greater than about 9.

18. The method of claim 17, wherein the carbon source is glucose.

19. The method of claim 1, wherein culturing the cell in the presence of the carbon source comprises culturing the cell in the presence of a carbon source and a non-hydrolyzable glucose analog.

20. The method of claim 18, wherein the non-hydrolyzable glucose analog is methyl glucopyranoside.

21. The method of claim 20, wherein the methyl glucopyranoside is present in an amount of from about 0.5 mM to about 1.0 mM.

* * * * *

UNITED STATES PATENT AND TRADEMARK OFFICE
CERTIFICATE OF CORRECTION

PATENT NO. : 6,472,169 B1
DATED : October 29, 2002
INVENTOR(S) : John W. Frost et al.

It is certified that error appears in the above-identified patent and that said Letters Patent is hereby corrected as shown below:

Column 2,
Line 58, "ptsipSC6.090B" should be -- pts$^-$/pSC6.090B --.

Column 4,
Line 5, "arok-encoded" should be -- aroK-encoded --.
Line 12, "arok" should be -- aroK --.

Column 5,
Line 12, "theptsH" should be -- the ptsH --.
Line 27, "arok-encoded" should be -- aroK-encoded --.
Line 31, "w i b e" should be -- will be --.
Line 60, "TTeaty" should be -- Treaty --.

Column 8,
Line 32, delete "15".

Column 9,
Line 50, "PpsP$_{tac}$" should be -- ppsP$_{tac}$ --.

Column 14,
Line 11, "E. col" should be -- E. coli --.

Column 17,
Line 65, after "were" delete "5".

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,472,169 B1
DATED        : October 29, 2002
INVENTOR(S)  : John W. Frost et al.

It is certified that error appears in the above-identified patent and that said Letters Patent is hereby corrected as shown below:

<u>Column 6,</u>
Line 16, Table 1. d), "3)-dehydroshikimate" should be -- shikimate --.

<u>Column 18,</u>
Lines 49 and 63, "3-dehydroshikimate" should be -- shikimate --.

Signed and Sealed this

Second Day of August, 2005

JON W. DUDAS
*Director of the United States Patent and Trademark Office*